(12) United States Patent
Joung et al.

(10) Patent No.: US 8,729,340 B2
(45) Date of Patent: May 20, 2014

(54) SOLANUM LYCOPERSICUM HISTIDINE DECARBOXYLASE GENE-DERIVED FRUIT-SPECIFIC EXPRESSION PROMOTER AND USES THEREOF

(75) Inventors: Young Hee Joung, Daejeon (KR); Ah Young Kim, Gwangju (KR); Sang Hyeob Lee, Daejeon (KR)

(73) Assignee: Industry Foundation of Chonnam National University, Gwangju (KR)

( * ) Notice: Subject to any disclaimer, the term of this patent is extended or adjusted under 35 U.S.C. 154(b) by 222 days.

(21) Appl. No.: 13/148,949

(22) PCT Filed: Feb. 11, 2010

(86) PCT No.: PCT/KR2010/000849
§ 371 (c)(1),
(2), (4) Date: Aug. 11, 2011

(87) PCT Pub. No.: WO2010/093174
PCT Pub. Date: Aug. 19, 2010

(65) Prior Publication Data
US 2011/0321188 A1 Dec. 29, 2011

(30) Foreign Application Priority Data

Feb. 12, 2009 (KR) .................. 10-2009-0011585

(51) Int. Cl.
| | |
|---|---|
| *C12N 15/82* | (2006.01) |
| *A01H 5/00* | (2006.01) |
| *C07H 21/04* | (2006.01) |
| *C12N 15/00* | (2006.01) |
| *C12N 1/21* | (2006.01) |

(52) U.S. Cl.
USPC ....... 800/287; 800/298; 536/24.1; 435/320.1; 435/252.2

(58) Field of Classification Search
None
See application file for complete search history.

(56) References Cited

U.S. PATENT DOCUMENTS 4,940,838 A    7/1990   Schilperoort et al.

FOREIGN PATENT DOCUMENTS

| EP | 0120516 A2 | 10/1984 |
| EP | 0301316 A2 | 2/1989 |
| KR | 10-2005-0035314 A | 4/2005 |
| KR | 10-0784165 B1 | 12/2007 |
| WO | WO 93/07257 | * 4/1993 |

OTHER PUBLICATIONS

Picton et al., Plant Mol Biol 23:627 (1993).*
Kim_Plant Biol Rockville_109_2008.*
Komarnytsky Genetic Engin_25_113_2003.*
Albert et al. J Exp Bot. 59(10): 2673-2686. Published online May 31, 2008.
Giovanni Levia. EMBO Rep. Nov. 15, 2000; 1(5): 378-380.
Mason et al., Proc Natl Acad Sci USA. May 28, 1996; 93(11): 5335-5340.
Krens, F.A. et al., 1982, Nature 296, 72-74.
Negrutiu I. et al., Jun. 1987, Plant Mol. Biol. 8, 363-373.
Shillito R.D. et al., 1985 Bio/Technol. 3, 1099-1102.
Crossway A. et al., 1986, Mol. Gen. Genet. 202, 179-185.
Klein T.M. et al., 1987, Nature 327, 70.
Genetica 133:207-214 (Zhu-Mei He) 2007, "Assessment of the utility of the tomato fruit-specific E8 promoter for driving vaccine antigen exression".
Clinical and Vaccine Immunology 14(6):685-692 (Ramirez) 2007, "Fruit-Specific Expression of the Human Immunodeficiency Virus Type 1 Tat Gee in Tomato Plants and Its Immunogenic Potential in Mice".
In Vitro Cell. Dev. Biol. Plant: 37:427-433 (Krasnyanski) 2001, "Effect of an enhanced CAMV 35S Promoter and Fruit-Specific Promoter on UIDA Gene Expression in Transgenic Tomato Plants".
J of American College of Nutrition 21(3):212S-217S (Korban) 2002, "Food as Production and Delivery Vehicles for Human Vaccines".
Englsih Abstract of KR10-0784165, (2010).
Englsih Abstract of KR10-2005-0035314, (2005).
International search Report for PCT/KR2010/000849, (2011).

* cited by examiner

*Primary Examiner* — Medina A Ibrahim
*Assistant Examiner* — Russell Boggs
(74) *Attorney, Agent, or Firm* — The PL Law Group, PLLC

(57) ABSTRACT

The present invention relates to a *Solanum lycopersicum* histidine decarboxylase-2 (SlHD-2) gene-derived fruit-specific expression promoter, to a 5' untranslated region (5'-UTR), to a (5'UTR), —specific expression vector comprising same, to a method for the fruit-specific expression of an exotic gene using the expression vector, to a plant transformed with the expression vector, and to a seed thereof. According to the present invention, a gene introduced from a transformed plant can be specifically expressed fruit tissue as compared to the widely used conventional Cauliflower mosaic virus-derived CaMV 35S promoter which induces the expression of an exotic gene in the whole tissue. Further, the present invention can be valuably used in the development of a transformed plant, which seeks to produce valuable substances from fruit.

12 Claims, 7 Drawing Sheets

FIG. 3

```
-784  AGCCACTATATTTATTTTACATTATTAATTTGCCATTTTA  -745
       CAT-box
-744  TATAATTATTCCAATACAATTAAATTTCCACAAAATTTAA  -705
-704  GTGTGCAATCGACAAAATAAATGAGACATGAAGGGAGTGT  -665
-664  TTGGTAAAACGAAAAATGTTTTTCATATAAGAATGCCTTT  -625
-624  TAGAATAAGTGGGTTATTTTTTTATTTTTTATTTTGTATT  -585
-584  TAGTACATAATTATTTTTTTTCATCTTAAACATGTATTAT  -545
-544  TAAATATAATTTAAATAAAAACTATGAGAGATGAAGATAG  -505
-504  AGGGACGGGGATGAAGATGAGGTGCATTGAAAGGTGTGGA  -465
-464  TTACTACCAATTAAAATGTTAGTAACTTGTTTTCCCAACT  -425
-424  TTCATTAATTATTCCCTATTTTTTTAAAGAATTGACGAAC  -385
                                        TGACG-motif
-384  TGAACCTAAGACTCCTATCTCCTAATTATTAAGGGAGAAA  -345
-344  AAATGAAATATTTTTTCAAGTTTACGTTATTTTCAAAGTT  -305
-304  TTAGATATTTTCCGTTAACATGTTCAACATAACAGTGATG  -265
-264  AAATTTAAGATTCACCACACAAAAGTTAAGAAGGCAAAGC  -225
-224  AATTTTTGTTGTTATAAATTGAAGGTTCCAAGGATAATGA  -185
-184  GACTCACAAAACTTTTATCTCTTTAATTTGAGGCAATTAT  -145
-144  TCTCATCTCAAATTATTACAATTTTTAGCTCTATTAGGAT  -105
-104  GGGAACTGAAAGTGTACGTAATATTTATGCTCAATTTTCT   -65
                                          CAAT box
-64   AGTTTTCTCTTTTATATACTCATTCATTCATTTTAAATCA   -25
                                           TATA box
-24   TACTAGTACATTATATATTAAATT                    -1
+1     4rd GSP2         5'-UTR     TTAATTTTTTGTGTGA  +16
+17   TTATGAAATAGGAATTTGACTCAACAGTAGTCGCAACAAA   +56
+57   AACTGGAATCAACGCACCATTGTCATCTCCAAGGGACAAT   +96
      4rd GSP1
+97   ATGTGTCTTAGTTTGATTGAACCTCATATTAAGAATAAAA  +136
+137  CATCTTCCGAAGAATTGAAC                      +156
              +542 ~ +910    +1811~ +1869   +2629~ +2649
+157  ATG-----3rd GSP2~GSP1------2rd GSP2~GSP1-------1rd GSP2~GSP1--------
      Start codon
```

FIG. 7
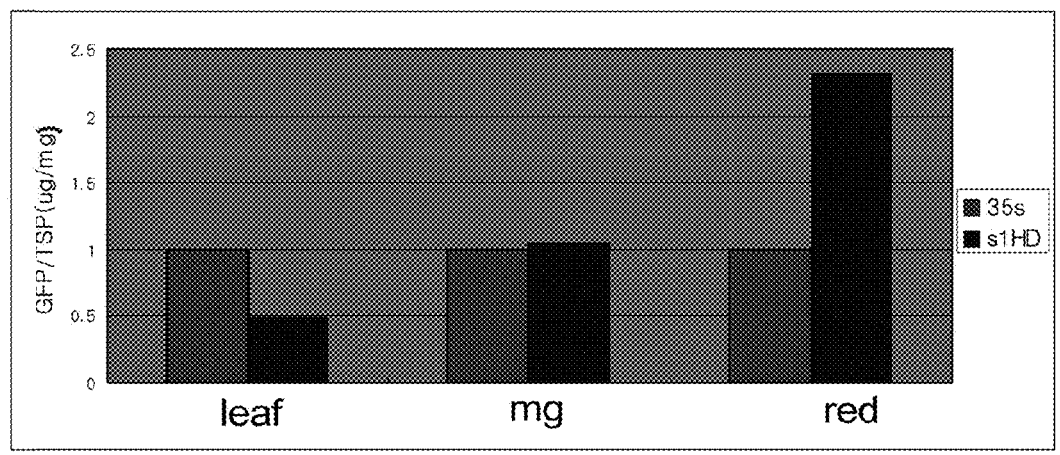
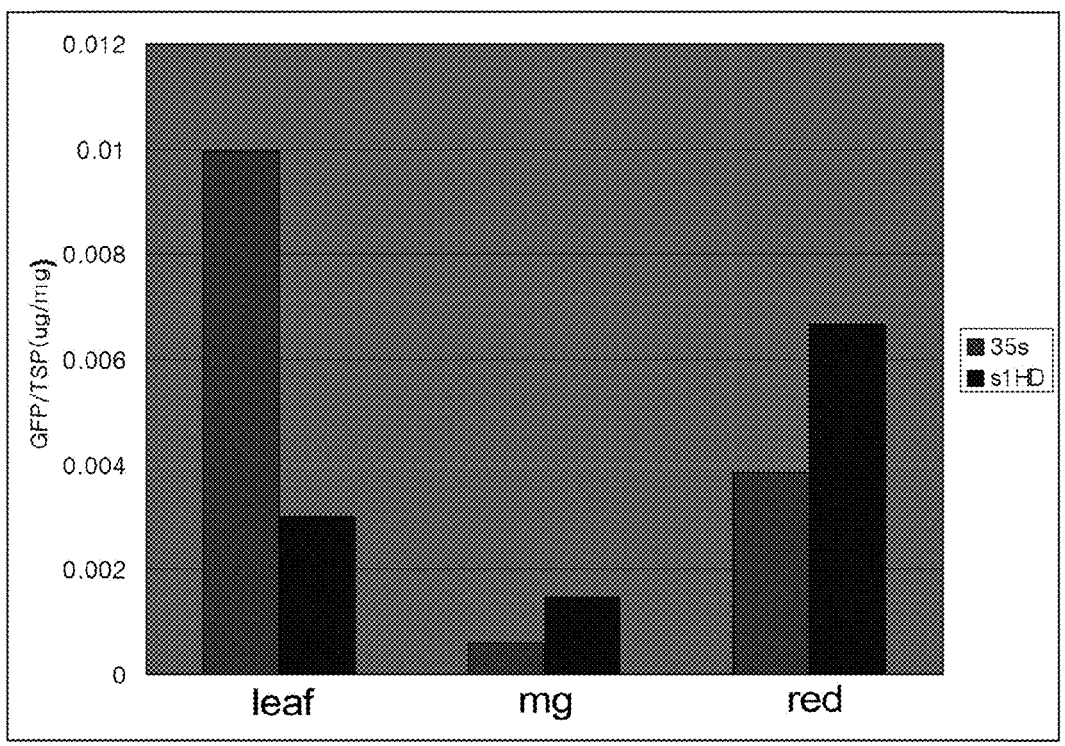

SOLANUM LYCOPERSICUM HISTIDINE DECARBOXYLASE GENE-DERIVED FRUIT-SPECIFIC EXPRESSION PROMOTER AND USES THEREOF

CROSS REFERENCE TO RELATED APPLICATION

The present application claims all benefits accruing under 35 U.S.C. §365(c) from the PCT International Application PCT/KR2010/000849, with an International Filing Date of Feb. 11, 2010, which claims the benefit of Korean patent application No. 10-2009-0011585 filed in the Korean Intellectual Property Office on Feb. 12, 2009, which claims the priority the entire contents of which are incorporated herein by reference.

BACKGROUND

1. Field of the Invention

The present invention relates to a fruit-specific expression promoter from *Solanum lycopersicum* histidine decarboxylase gene and uses thereof. More specifically, the present invention relates to a fruit-specific expression promoter and 5'-untranslated region (herein below, abbreviated as "5'-UTR") from *Solanum lycopersicum* histidine decarboxylase gene, a plant fruit-specific expression vector comprising the same, a plant transformed with the expression vector, a process for fruit-specific expression of a foreign gene by using the expression vector, and a transformed plant which expresses a foreign gene in a fruit-specific manner according to the process and seeds of the transformed plant.

2. Background Art

According to recent research trends, it is found that more studies are made on expression of a substance in plant as an eukaryotic organism compared to expression in bacteria as a prokaryotic organism. Such change is based on the fact that the substance obtained from a plant as an eukaryotic organism can be extracted more stably and occurrence of a possible change in the substance during a process like glycosylation is lower compared to bacteria (Albert et al., J Exp Bot. 59(10): 2673-2686. Published online 2008 May 31).

Previously developed 35S promoter is a very useful promoter having high efficiency for expression in every part of a dicot plant tissue, and thus it can be used most effectively for gene expression in plant. However, from the viewpoint of achieving expression of a specific substance in a desired tissue by transformation, a load to the plant is quite heavy as it involves with unnecessary expression. As such, a study to reduce unnecessary expression in stalk or leaf of a plant from which only a fruit is taken, for example a tomato, and to achieve specific expression in the fruit only is required. Tomato is one of the best candidates to study plants and, as the entire fruit flesh is eaten, its importance as a source for obtaining a certain substance by over-expression and intaking it as a raw or cooked material, or as a vaccine is being realized. From this point of view, it was confirmed recently that the tomato fruit is a good material for development of an oral vaccine (Giovanni Levia. EMBO Rep. 2000 Nov. 15; 1(5): 378-380). According to various recent studies related to vaccine, development of a vaccine using a crop like potato or sweet potato is widely carried out and a commercially available vaccine product has been already developed (Mason et al., Proc Natl Acad Sci USA. 1996 May 28; 93(11): 5335-5340). In this connection, it is aimed in this study to achieve fruit-specific expression of a substance based on development of a promoter which is overexpressed in a fruit-specific manner.

Since a fruit like a tomato can be eaten only after it is fully matured, if expression of a substance starts from a fruit at early-maturing period and is maintained until the late-maturing period, a great amount of the substance will accumulate in the fruit. To obtain such effect, a gene showing a certain level of expression or increasing expression during maturing period needs to be selected.

The inventors of the present invention selected, based on a microarray method, a gene which shows increasing or constant expression from the mature green stage to the red stage of a tomato fruit. Among the genes selected, the *Solanum lycopersicum* histidine decarboxylase gene was chosen as it showed the most favorable expression efficiency. Since expression of this gene is accumulated during a maturing process of a tomato fruit, i.e., its accumulation starts from the start of braking and is involved with ripening of a tomato fruit, it was believed that the gene may be also appropriate as a sought-after promoter having good expression efficiency.

Meanwhile, in Korean Patent Reg. No. 0784165, a promoter which regulates UDP-glucosyltransferase originated from a pepper, that is related to resistance of pepper plant against pathogenic infection and maturing process of a pepper fruit, is disclosed, and in Korean Patent Reg. No. 0574563, a highly efficient expression promoter from *Arabidopsis thaliana* and an expression vector comprising the promoter for highly efficient expression in plant are disclosed. However, these promoters are different from the promoter of the present invention.

SUMMARY

The present invention, which is devised in view of the necessities described in the above, is based on the finding that, when the promoter and 5'-UTR of the *Solanum lycopersicum* histidine decarboxylase gene are cloned, inserted to a binary vector, and then introduced to *Solanum lycopersicum*, the foreign gene is expressed specifically in a fruit tissue of *Solanum lycopersicum*. Consequently, the present invention was completed.

In order to solve the problems described in the above, the present invention provides a fruit-specific plant expression promoter or 5'-UTR that are derived from *Solanum lycopersicum* histidine decarboxylase gene.

Further, the present invention provides a fruit-specific plant expression promoter vector which comprises the above described fruit-specific plant expression promoter and/or 5'-UTR, and a plant which is transformed with the expression vector.

Further, the present invention provides a process for fruit-specific expression of a foreign gene by using the above described fruit-specific expression promoter or 5'-UTR, when a useful substance is desired to be produced in large scale in a plant fruit.

Still further, the present invention provides a transformed plant prepared based on the process above and seeds of the transformed plant, wherein the transformed plant expresses a foreign gene in a fruit-specific manner.

According to the present invention, with expression of a foreign gene in a plant using the fruit-specific expression promoter and/or 5'-UTR derived from *Solanum lycopersicum* histidine decarboxylase gene, it was found that the promoter of the present invention is a novel promoter which can express a gene specifically in a plant fruit.

BRIEF DESCRIPTION OF THE DRAWINGS

FIG. 3 illustrates the sequence of SlHD-2 promoter located upstream of 5' flanking region of transcription initiation site (+1). UTR; untranslated region.

FIG. 7 illustrates the results of analyzing the SlHD-2 promoter activity. The transient expression by Agro-infiltration shows that the relative expression level of GFP having SlHD-2 promoter is comparable to CaMV 35S promoter in Solanum lycopersicum tissue. (A) GFP expression level when $^{35}$S-GFP is 1.00. (B) It indicates an average value.

DETAILED DESCRIPTION

Figure 1:
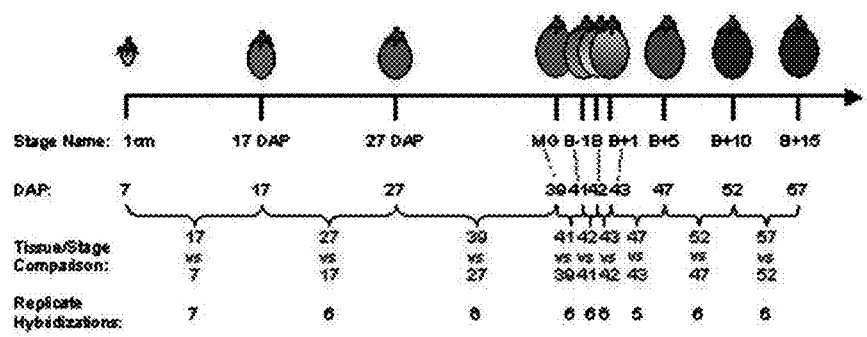
FIG. 1 illustrates the microarray data of SOL genomic network database. It includes (A) maturation process of a tomato and (B) profile analysis of a fruit-specific expression of a gene based on microarray data from SOL genomic network database (http://www.sgn.cornell.edu). DAP, days after pollination; MG, Mature green stage; B, Breaking stage.

In order to achieve the purpose of the invention as described in the above, the present invention provides a fruit-specific plant expression promoter which comprises a nucleotide sequence from nucleotide base number I to number 784 (i.e., −784 to −1, starting from the transcription initiation site) of the sequence shown in FIG. 3 (SEQ ID NO: 1).

Compared to CaMV35S promoter from cauliflower mosaic virus by which gene expression is promoted in entire tissues of a plant, the fruit-specific expression promoter of the present invention can be used for fruit-specific expression of a gene introduced to a transformed plant.

In order to achieve the purpose of the invention as described in the above, the present invention also provides 5'-UTR comprising the nucleotide sequence from nucleotide base number 785 to number 940 (i.e., +1 to +156, starting from the transcription initiation site) of the sequence shown in FIG. 3 (SEQ ID NO: 1).

In addition, a sequence variant of the above described promoter or 5'-UTR also falls within the scope of the present invention. The term "variant" means a nucleotide sequence which may have a different nucleotide sequence but has a similar functional characteristic compared to the nucleotide sequence of SEQ ID NO: 1. Specifically, the above described promoter sequence and 5'-UTR sequence may have a nucleotide sequence which has sequence homology of at least 70%, preferably at least 80%, more preferably at least 90%, still more preferably at least 95% compared to the nucleotide sequence of SEQ ID NO: 1.

Said "sequence homology %" for a certain polynucleotide is identified by comparing a comparative region with two sequences that are optimally aligned. In this regard, a part of the polynucleotide in comparative region may comprise an addition or a deletion (i.e., a gap) compared to a reference sequence (without any addition or deletion) relative to the optimized alignment of the two sequences.

In order to achieve another purpose of the present invention, the present invention provides a fruit-specific plant expression vector which comprises a fruit-specific plant expression promoter and/or 5'-UTR.

The fruit-specific plant expression vector of the present invention may comprise only the promoter of the present invention, or 5'-UTR of the present invention can be used in combination with other common plant expression promoter such as CaMV 35S promoter. Preferably, however, having both the promoter of the present invention and the 5'-UTR is advantageous for obtaining fruit-specific expression of a foreign gene introduced in a plant.

The fruit-specific plant expression vector of the present invention may be used as a transient expression vector which can transiently express a foreign gene in a plant or as a plant expression vector which can permanently express a foreign gene in a plant.

A binary vector which can be used for the present invention can be any binary vector comprising RB (right border) and LB (left border) of T-DNA which can transform a plant when it is present with Ti plasmid of A. tumefaciens. Preferably, pBI101 (Cat#: 6018-1, Clontech, USA), pBIN19 (Genbank Deposit No. U09365), pBI121, pCAMBIA and the like, which are often used by a skilled person in the pertinent art, are used.

Figure 4:
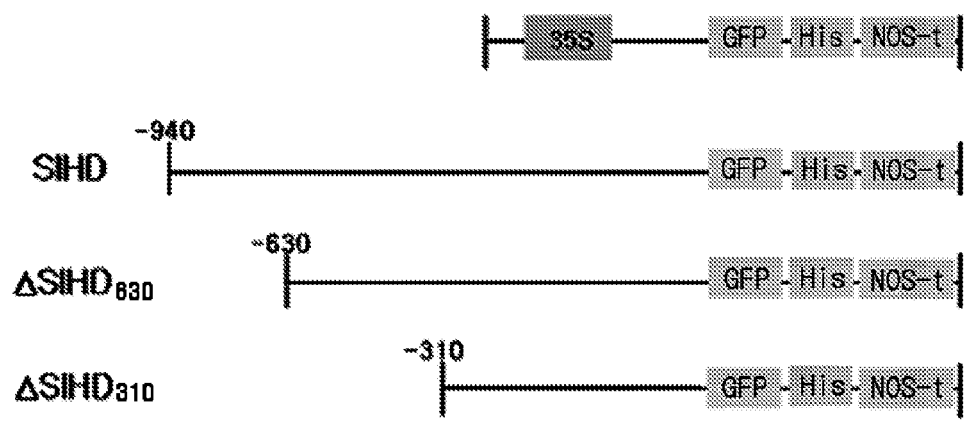
FIG. 4 illustrates a schematic diagram of a vector for analyzing promoter activity. pCAM-2300HD (SlHD) is a vector for full-length promoter, pCAM-2300HDΔ630 (ΔSlHD$_{630}$) and pCAM-23004310 (ΔSlHD$_{310}$) are for the partially deleted promoter, and pCAMBIA 1302 (35S) is a positive control for transient expression in Solanum lycopersicum. NOS-t; NOS terminator, 35S; CaMV35S promoter, GFP; green fluorescent protein encoding gene, His tag; hexa-histidine tail.

According to one embodiment of the present invention, a fruit-specific plant expression vector can be pCAM-2300HD depicted in FIG. 4, but not limited thereto. The promoter of the present invention is inserted into a binary vector (pCAMBIA 1391Z) used for analyzing a promoter to prepare pCAM-2300HD (FIG. 4), wherein GFP gene is comprised. Then, the vector is used for plant transformation using Agrobacterium. It would be obvious for a skilled person in the art that said GFP reporter gene can be replaced with other target foreign gene.

The term "vector" is used herein to refer DNA fragment(s) and nucleotide molecules that are delivered to a cell. Vector can be used for the replication of DNA and be independently reproduced in a host cell. The terms "delivery system" and "vector" are often interchangeably used. The term "expression vector" means a recombinant DNA molecule comprising a desired coding sequence and other appropriate nucleotide sequences that are essential for the expression of the operatively-linked coding sequence in a specific host organism. A promoter, an enhancer, a termination signal and a polyadenylation signal that can be used for an eukaryotic cell are all publicly well known.

A preferred example of plant expression vector is Ti-plasmid vector which can transfer a part of itself, i.e., so-called T-region, to a plant cell when the vector is present in an appropriate host such as *Agrobacterium tumefaciens*. Other types of Ti-plasmid vector (see, EP 0 116 718 B1) are currently used for transferring a hybrid gene to protoplasts that can produce a new plant by appropriately inserting a plant cell or hybrid DNA to a plant genome. Especially preferred form of Ti-plasmid vector is a so-called binary vector which has been disclosed in EP 0 120 516 B1 and U.S. Pat. No. 4,940,838. Other appropriate vectors that can be used for introducing the DNA of the present invention to a host plant can be selected from a double-stranded plant virus (e.g., CaMV), a single-stranded plant virus, and a viral vector which can be originated from Gemini virus, etc., for example a non-complete plant viral vector. Use of said vector can be especially advantageous when a plant host cannot be appropriately transformed.

Expression vector preferably comprises at least one selection marker. Said selection marker is a nucleotide sequence having a property which allows a selection based on a common chemical method. Any kind of gene that can be used for the differentiation of transformed cells from non-transformed cells can be a selection marker. Example includes, a gene resistant to herbicide such as glyphosate and phosphinotricin, and a gene resistant to antibiotics such as kanamycin, G418, bleomycin, hygromycin, and chloramphenicol, but not limited thereto.

With respect to a terminator for a plant expression vector of one embodiment of the present invention, any typical terminator can be used. Examples thereof include nopaline synthase (NOS), rice α-amylase RAmyl A terminator, phaseoline terminator, a terminator for octopine gene of *Agrobacterium tumefaciens* and the like, but not limited thereto.

In order to achieve another purpose of the present invention, the present invention provides *E. coli* or *Agrobacterium tumefaciens* that is transformed with the fruit-specific plant expression vector of the present invention.

In order to achieve another purpose of the present invention, the present invention provides a plant that is transformed with the fruit-specific plant expression vector of the present invention and seeds of the plant.

The fruit-specific plant expression vector of the present invention can be used for transformation of any plant including a dicot and a monocot plant. In the present invention, transformation was carried out using *Solanum lycopersicum*. The plant according to one embodiment of the present invention can be a dicot plant such as tomato, *Arabidopsis*, potato, eggplant, tobacco, pepper, burdock, crown daisy, lettuce, Chinese bellflower, chard, spinach, sweet potato, celery, carrot, coriander, parsley, Chinese cabbage, cabbage, leaf mustard, watermelon, melon, cucumber, zucchini, gourd, strawberry, soy bean, mung bean, kidney bean, sweet pea and the like.

Transformation of a plant means any method which can deliver a DNA to a plant. Such transformation is not necessarily required to have a period for regeneration and/or tissue culture. Transformation of a plant is now generally carried out not only for a dicot plant but also for a monocot plant. In principle, any method for transformation can be used for introducing a heterologous DNA of the present invention to a progenitor cell. Transformation can be carried out according to any method selected from a calcium/polyethylene glycol method for protoplasts (Krens, F. A. et al., 1982, Nature 296, 72-74; Negrutiu I. et al., June 1987, Plant Mol. Biol. 8, 363-373), an electroporation method for protoplasts (Shillito R. D. et al., 1985 Bio/Technol. 3, 1099-1102), a microscopic injection method for plant components (Crossway A. et al., 1986, Mol. Gen. Genet. 202, 179-185), a particle bombardment method for various plant components (DNA or RNA-coated) (Klein T. M. et al., 1987, Nature 327, 70), or a (non-complete) viral infection method in *Agrobacterium tumefaciens* mediated gene transfer by plant invasion or transformation of fully ripened pollen or microspore (EP 0 301 316), etc. According to the present method, *Agrobacterium* mediated DNA transfer is preferred. In particular, so-called binary vector technique as disclosed in EPA 120 516 and U.S. Pat. No. 4,940,838 can be preferably adopted for the present invention.

The "plant cell" that is used for the plant transformation according to the present invention can be any plant cell. The plant cell can be a cultured cell, a cultured tissue, a cultured organ, or a whole plant, preferably a cultured cell, a cultured tissue or a cultured organ, and more preferably any form of a cultured cell.

The "plant tissue" includes either differentiated or undifferentiated plant tissue, including fruit, stem, leaf, pollen, seed, cancerous tissue and cell lines having various shape that are used for culture, i.e., single cell, protoplast, bud and callus tissue, but not limited thereto. Plant tissue can be in planta or in a state of organ culture, tissue culture or cell culture.

In order to achieve another purpose of the invention, the present invention provides a process for fruit-specific expression of a foreign gene in a transformed plant comprising steps of:
  carrying out recombination of a foreign gene in the fruit-specific plant expression vector of the present invention, and
  transforming a plant with the recombinant fruit-specific expression vector.

Any gene which is desired to be expressed in a mass amount can be employed as a foreign gene. It is placed in the downstream region of the promoter in the fruit-specific plant expression vector of the present invention, and if necessary, it can be expressed as being fused with a reporter gene. Transformation of a plant with the recombinant fruit-specific expression vector of the present invention can be carried out according to the process as described in the above. The plant according to one embodiment of the present invention can be a dicot plant such as tomato, *Arabidopsis*, potato, eggplant, tobacco, pepper, burdock, crown daisy, lettuce, Chinese bellflower, chard, spinach, sweet potato, celery, carrot, coriander, parsley, Chinese cabbage, cabbage, leaf mustard, watermelon, melon, cucumber, zucchini, gourd, strawberry, soy bean, mung bean, kidney bean, sweet pea and the like.

In order to achieve yet another purpose of the invention, the present invention provides a transformed plant that is produced according to the process described above wherein a foreign gene is expressed in a fruit-specific manner, and seeds of the plant. The transformed plant can express a foreign gene in a fruit-specific manner with an aid of a fruit-specific expression promoter and/or 5'-UTR.

The present invention will now be described in greater detail with reference to the following examples. However, it is only to specifically exemplify the present invention and in no case the scope of the present invention is limited by these examples.

Materials and Methods

1. Plant Material

Tomato (*Solanum lycopersicum* cv. Micro-Tom) plant was kept in an incubator at 24° C.

2. Isolation of Genomic DNA of *Solanum lycopersicum* and Genome Walking PCR for Identifying 5'-Upstream Region To extract genomic DNA from *Solanum lycopersicum*, leaf tissue of the plant was finely ground by using liquid nitrogen, and extracted according to the protocol of DNeasy plant mini kit (Qiagen, Germany). After that, 2.5 ug of the genomic DNA was treated with 80 unit of DraI, EcoRV, PvuII, or StuI at 37° C. for 16 hrs or more to generate a blunt end. After purification with phenol:chloroform (1:1), the DNA was recovered by using 100% ethanol and dissolved in 20 ul sterile water. 4 ul of the resultant was subjected to ligation with Genome Walker Adaptor fragment (Clontech, USA). Primary PCR was performed by using Adapter primer 1 (AP1) and SlHD gene-specific primer 1 (GSP 1). Composition of the reaction is as follows: DNA polymerase buffer; 1.5 mM Mg(OAc)$_2$, 2.5 mM of each dNTP (dATP, dTTP, dCTP, dGTP), 10 pM of each primer (AP1 and SlHDGSP1); 1 ul ligated DNA as a template, and 0.1 U DNA polymerase. Condition for the primary PCR includes seven cycles of 25 sec at 94° C. and 3 min at 72° C., followed by 32 cycles of 25 sec at 94° C. and 3 min at 67° C. After one additional cycle of 7 min at 67° C., the temperature was lowered to 4° C. to terminate the reaction. Product of the primary PCR was diluted (×1/50), and then the nested secondary PCR was carried out by using AP2 and GSP2. The reaction composition was the same as the reaction composition of the primary PCR. Condition for the nested secondary PCR includes fives cycles of 25 sec at 94° C. and 3 min at 72° C., followed by 20 cycles of 25 sec at 94° C. and 3 min at 67° C. After one additional cycle of 7 min at 67° C., the temperature was lowered to 4° C. to terminate the reaction. Sequence of the primers used for the PCR is given in Table 1. To verify the PCR result, electrophoresis was performed by using 1% agarose gel.

3. Preparation of DH5α/*E. Coli* Competent Cell (CP Cell) and Transformation

*E. coli* cell DH5α was inoculated to 3 ml of LB medium (peptone 10 g/L, yeast extract 5 g/L, and NaCl 10 g/L, pH 7.2) and cultured at 37° C. under shaking for 18 hours or more. After several passages in 100 ml LB liquid medium, the cells were further cultured until O.D. value of 0.4 to 0.45. The culture was kept on ice for 15 min and centrifuged for 20 min at 4° C., 4000 rpm to recover the cells. The recovered *E. coli* was treated with ice-cold 80 mM MgCl$_2$-20 mM CaCl$_2$ solution. After keeping on ice for 15 min, the cells were centrifuged for 20 min at 4° C., 4000 rpm, treated with 2 ml of 0.1M ice-cold CaCl$_2$ solution, and then used for transformation. For immediate use, the cells were kept on ice for 30 min and then used. For other cases, 15 to 20% glycerol was added to the cells, which were then kept at −70° C.

After mixing the competent cells with the DNA, the mixture was kept on ice for 30 min or more, and then subjected to heat shock for 90 sec at 42° C. The cells were added with 1 ml of LB liquid medium not containing antibiotics followed by culture for 1 hour at 37° C. Thereafter, by inoculating to LB medium containing antibiotics, transformed colonies were selected. After culture, plasmid was isolated from the selected colonies by using Accup prep. mini kit (Bioneer, Korea), and then confirmed by using a restriction enzyme.

4. Preparation of *Agrobacterium* Competent Cells and Transformation

*Agrobacterium* cells were inoculated to 5 ml of YEP liquid medium (yeast extract 10 g/L, peptone 10 g/L, NaCl 5 g/L, pH 7.2) and cultured under shaking at 28° C. After several passages of 1 ml culture in 50 ml YEP liquid medium, the cells were further cultured until O.D. (600 nm) value of 0.6 to 1.0. The culture was kept on ice for 30 min and centrifuged for 20 min at 4° C., 4000 rpm, re-suspended in 0.15M ice cold NaCl solution, and then kept on ice for 10 min. The cells were centrifuged again for 20 min at 4° C., 4000 rpm, and the recovered pellet was re-suspended in 20 mM CaCl$_2$ (1 ml), and then aliquoted 50 ul each. The aliquots were rapidly frozen in liquid nitrogen and stored at −70° C.

The stored competent cells were mixed with 1 ug of DNA, frozen for 2 min in liquid nitrogen, and then subjected to heat shock treatment for 5 min at 37° C. After brief mixing, this process was repeated one more time. After keeping on ice for 30 min, the cells were added with 1 ml YEP liquid medium, and cultured for 2 hours at 28° C. The cells were then applied to YEP solid medium containing Rif (50 mg/L) and Km (50 mg/L), and then transformed colonies were selected.

5. Recombinant Vector for SlHD Promoter Region 1 kb SlHD promoter region was identified by genome walking PCR. After PCR using SlHD F primer and SlHD R primer, it was digested with HindIII and BamHI enzymes for recombination with pCAMBIA1391Z. Ligation was then carried out by using T4 ligase at 24° C. for 3 hours. Identification was made with transformation of DH5α/*E. coli* competent cells and selection on LB+Km 50 mg/L agar plate followed by digestion with HindIII and BamHI. The plasmid was extracted and used for transformation of *Agrobacterium* LBA4404 competent cells. Selection was made by using YEP+Rif 50 mg/L+Km 50 mg/L agar plate, and the selected cells were used for plant transformation by Agro-infiltration.

To perform transient expression assay of *Solanum lycopersicum*, recombination of the SlHD promoter region to pCAMBIA2300 vector in which GFP is fused was carried out, and the resultant was used for transformation of *Agrobacterium* strain LBA4404 competent cells. Further, to confirm the function and expression level of a cis-acting element, recombination of the SlHD promoter region into −480/+156 region and −155/+156 region was carried out for deletion test. Specifically, for each region (full length), ΔSlHD630 primer and ΔSlHD310 primer were subjected to PCR with SlHD reverse primer followed by digestion with HindIII and BamHI for recombination into pCAMBIA2300-GFP. The resulting vector was used for transformation of *Agrobacterium* strain LBA4404 competent cells. Sequence of the primers used for cloning is given in Table 1.

6. RNA Extraction and Real Time PCR

RNA was extracted to be used for real time PCR. From the *Solanum lycopersicum* fruit (0.5 cm diameter) harvested at each stage of green, mature green, breaking and red ripe and the leaves, 50 mg sample was taken by using TRI reagent, finely homogenized, and used. Specifically, after homogenizing 50 mg plant tissue, 1 ml TRI reagent was added. After vortexing, the sample was kept at room temperature for 5 min. 0.2 ml chloroform was added and vigorously mixed. After keeping at room temperature for 15 min, the sample was centrifuged at 4° C., 12000 rpm for 15 min. The aqueous phase (0.5 ml) was transferred to a new tube, added with 0.5 ml isopropanol, and mixed well. After keeping at room temperature for 10 min, the sample was centrifuged at 4° C., 12000 rpm for 15 min. The supernatant was discarded and only the RNA pellet was washed with 75% EtOH (0.5 ml). The resulting pellet was fully dissolved in water (20 ul) added with DEPC.

For RT-PCR, the RNA extracted before was used. 1 ug of RNA was weighed, mixed with each primer, and then used for the test. SYBR Green Master Mix kit was used (QuantiTect SYBR Green PCR Handbook. WWW.QIAGEN.COM). For carrying out real time PCR program, heat denaturation was performed for 15 min at 94° C., and 40 cycles including cycle condition of one min at 94° C., another minute at 52° C., and 30 sec at 72° C. were performed. As a primer, SlHD exon and 3'-UTR specific primer set was prepared and used. As a positive control, the primer for *Solanum lycopersicum* actin gene was used for amplification by PCR and used.

7. Southern Blot Hybridization 20 ug of *Solanum lycopersicum* genomic DNA was used. SlHD-2 gene promoter was amplified by PCR by using the 5' upstream 360 bp DNA which has been newly identified by using a known gene with Southern blot DIG probe synthesis kit (Rochi). After the identification, the product was subjected to Southern blot analysis. By using the primer which has been already prepared before loading the DNA, DIG probe was synthesized. Whole genomic DNA was extracted from the leaf of *Solanum lycopersicum*. 20 ug of the DNA was treated with HindIII and EcoRI, and then loaded on 0.8% agarose gel. Electrophoresis was carried out for 5 hours at 25V. After finishing the electrophoresis, the DNA in the gel was transferred to a cellulose membrane (Hybond N+, Amersham) by using vacuum and hybridized. The membrane (Hybond N+, Amersham) was overlaid on the gel which is placed on a vacuum apparatus. While running the apparatus, 30 ml of 0.25 M HCl was poured over the gel and the reaction was carried out for 10 min. The denaturation solution (0.4N NaOH, 50 ml) was poured and reacted for 20 min. The neutralization solution (0.2M Tris-HCl pH 7.5, 50 ml) was poured and reacted for 20 min. Next transfer process was carried out for 2 hours by filling the transfer solution every 30 min. The test was carried out according to the detection by using the DIG probe antibody followed by chromogenic reaction. For hybridization, pre-hybridization was carried out for 1 hour by using the hybridization solution (5×SSC, 0.02% SDS, 0.1% N-lauroylsarcosine Na-salt, 1% blocking reagent). After that, the pre-hybridization solution was discarded and the DNA probe labeled with the DIG was filled with the probe solution (25 ml). After 24 hours, the probe solution was removed, and washing was carried out for 5 min at room temperature by using 2×SSC, 0.1% SDS solution. After replacing the solution with 2×SSC, 0.5% SDS solution (20 ml), washing was carried out twice for 15 min at the same temperature as the pre-hybridization. For the immunological detection, the sample was washed at room temperature for 5 min by using the washing buffer (0.1M maleic acid, 0.15M NaCl pH 7.5, 0.3% Tween 20). After adding 10× blocking solution (blocking reagent, maleic acid buffer) and maleic acid buffer (0.1M maleic acid, 0.15M NaCl, pH was adjusted to 7.5 with NaOH) at the ratio of 1 to 9, the mixture was incubated at room temperature for 30 min. To the blocking buffer mixed at 1 to 9 ratio, anti-digoxigenin-AP (4 ul anti-digoxigenin-AP for 20 ml blocking buffer) was added and reacted at room temperature for 30 min. Upon the completion of the reaction, the mixture was washed twice with washing buffer (100 ml) for 15 min at room temperature. Next, the mixture was treated with the detection buffer (0.1M Tris-HCl, 0.1M NaCl, 20 ml) for 5 min at room temperature. To the detection buffer, 200 ul NBT/BCIP (200 ul NBT/BCIP/detection buffer, 10 ml) was added. The reaction was performed at room temperature for 16 hours or more.

8. Transient Expression Assay

For carrying out the transient expression assay, *Agrobacterium* LBA4404 cells were pre-cultured and passaged in YEP liquid medium (20 ml) comprising 200 uM acetosyringone. After culturing the cells until O.D=~0.7, the cells were recovered by centrifuge at 4500 rpm/4° C. for 20 min and re-suspended in ½ MS medium (MS 2.2 g, 2% sucrose, pH 5.7, 20 ml) added with 200 uM acetosyringone. *Agrobacterium* infection was carried out by injecting the cells into the seeds of *Solanum lycopersicum* to allow the agrofiltration into the tissues of leaf and fruit. The sample was harvested 2.5 days later, ground well with a protein extraction buffer (PEB), and centrifuged for 30 min at 15000 rpm/4° C. After that, the expression amount was determined by ELISA using the His-tagged monoclonal antibody. With reference to the expression amount of GUS protein expressed in *Agrobacterium* cell itself, the obtained values were normalized.

9. ELISA (Enzyme-Linked Immunosorbent Assay)

The sample was homogenized with a protein coating buffer (PCB, 3.3 g/L $Na_2CO_3$, 6.0 g/L $NaHCO_3$, pH 9.6) and centrifuged at 4° C., 15000 rpm. The supernatant was aliquoted 100 ul each to 96-well microplate and kept at room temperature for 2 hours. After washing with the protein extraction buffer (PEB, 1.16 g/L $Na_2HPO_4$, 0.1 g/L KCl, 0.1 g/L $K_3PO_4$, 4.0 g/L NaCl, pH 7.4), 200 ul of the blocking buffer (5% skim milk) was added to each well and kept for 2 hours at room temperature. Thereafter, the plate was washed twice with PEB and aliquoted with 50 ul of the primary antibody (Novagen, Germany) which has been diluted to $10^{-7}$. It was then kept at room temperature for 2 hours to allow the desired interaction among proteins. After that, the plate was washed with PEB for four or more times and aliquoted with 50 ul of the secondary His-tagged monoclonal antibody (Sigma, USA) which has been diluted to PEB at 1:2000 ratio. The mixture was maintained at room temperature for 1 hour for the reaction. After washing four times with PEB, the substrate solution (BD bioscience, USA, 50 ul) was aliquoted to each well. After maintaining at room temperature for 30 min, 50 ul of the stop solution (2.5M $H_2SO_4$) was added to terminate the reaction. The absorption at 450 nm was measured (Konrad Birkhaug. Am J Public Health Nations Health. 1950 May; 40(5): 545-554).

Example 1

Selection of a Gene with Fruit-Specific Expression

From the results obtained from microarray of *Solanum lycopersicum* of SOL genomic network database (http://www.sgn.cornell.edu), total 11 genes showing increased expression in accordance with the fruit ripening were selected (FIG. 1). A primer for amplifying the 3' UTR region and exon region of the selected gene was prepared and used for RT-PCR to determine the actual expression rate of mRNA in the fruit. As a result, it was found that expression of the genes of *Solanum lycopersicum* Histidine decarboxylase-1, -2 (SlHD-1, SlHD-2) and lipoxygenase, Guanine nucleotide-Binding protein beta subunit (GBB) was gradually increased from the mature green stage to the red ripe stage.

Example 2

Genome Walking

By using genome walking PCR, the promoter region was determined in the eleven genes obtained by microarray analysis. First, by using the genetic information already known, GSP1 and GSP 2, i.e., a gene specific primer, were produced. By using the primers and the adapter specific primer AP1 and AP2 included in the genome walking kit, PCR was carried out for genome walking library. From the SlHD-1, SlHD-2, and GBB genes, a putative promoter region having about 1 kb or more was isolated. Activity of the putative promoter isolated from the preliminary test was determined in *Solanum lycopersicum* fruit according to a transient expression assay. As a result, only the SlHD-2 promoter exhibited fruit-specific expression profile. The primer set used for genome walking PCR of the SlHD-2 gene was shown in Table 1. In Table 1, the GSP and AP primer were used for genome walking PCR, while SlHD Fwd/Rvs, ΔSlHD630, and ΔSlHD310 primers were used for amplification of a full-length or partially deleted promoter region. Fwd/Rvs primer was used for real time PCR analysis.

tively. Further, from the nucleotide sequence of SlHD-2 promoter, cis-acting elements like CAT box at −780 and TGACG box at −390 were identified (see, FIG. 3).

Example 3

SlHD-2 Gene Expression in *Solanum lycopersicum* Tissue

RNA was extracted from tissues of leaf, seed, stalk, flower and fruits at each maturing stage of *Solanum lycopersicum*, and then subjected to PCR and RT-PCR. As a result, it was found that SlHD-2 expression level is lower than actin in every tissue except the fruit at red ripe stage. However, its expression amount gradually increased according to maturation of the fruit, and it showed the highest expression at the red

TABLE 1

Primers for isolation of SlHD-1 promoter

Genome walking PCR primers

| | | |
|---|---|---|
| AP1 | | 5'-GTAATACGACTCACTATCGGGC-3' (SEQ ID NO: 2) |
| AP2 | | 5'-ACTATAGGGCACGCGTGGT-3' (SEQ ID NO: 3) |
| 1 Pound PCR | GSP1 | 5'-AATGCCACAAGGCATTGGACATCCCAA-3' (SEQ ID NO: 4) |
| | GSP2 | 5'-CATCCCAAGAATTTGTGCCCTGAAATTG-3' (SEQ ID NO: 5) |
| 2 Round PCR | GSP1 | 5'-ATGGAGATTGCCCTCAGTGCCACCAC-3' (SEQ ID NO: 6) |
| | GSP2 | 5'-CTGTAGGGTGCTGAGTAAAGGGGTCTCCAC-3' (SEQ ID NO: 7) |
| 3 Round pcR | GSP1 | 5'-GAGGAGAGAGGCGAGCGAGAGAGGGT-3' (SEQ ID NO: 8) |
| | GSP2 | 5'-TCTCTATCTCCATGCGGTAGAGGTTGTGTCTT-3' (SEQ ID NO: 9) |
| 4 Round PCR | GSP1 | 5'-CGTTGATTCCAGTTTTTGTTGCGAC-3' (SEQ ID NO: 10) |
| | | 5'-AATTTAATATATAATGTACTAGTATGATTT-3' (SEQ ID NO: 11) |

Full length primers

| | | |
|---|---|---|
| SlHD | Fwd | 5'-T<u>AAGCTT</u>AGCCACTATATTTATTTTAC-3' (SEO ID NO: 12)<br>HindIII |
| | Rvs | 5'-A<u>GGATCC</u>GTTCAATTCTTCGGAAGATG-3' (SEQ ID NO: 13)<br>BamHI |

Deletion test primers

| | |
|---|---|
| ΔSlHD630 | 5'-TAAGCTTCATTGAAAGGRGRGGAT-3' (SEQ ID NO: 14) |
| ΔSlHD310 | 5'-TAAGCTTGAGGCAATTATTCTCATC-3' (SEQ ID NO: 15) |

Real-Time PCR primers

| | |
|---|---|
| Fwd | 5'-CATTGCGATGCAGCATTATGTG-3' (SEO ID No): 16) |
| Rvs | 5'-TTCAAGTCATGGTRTCCAAGGAGT-3' (SEQ ID NO: 17) |

* Underlined indicates a restriction enzyme site.

Figure 2:
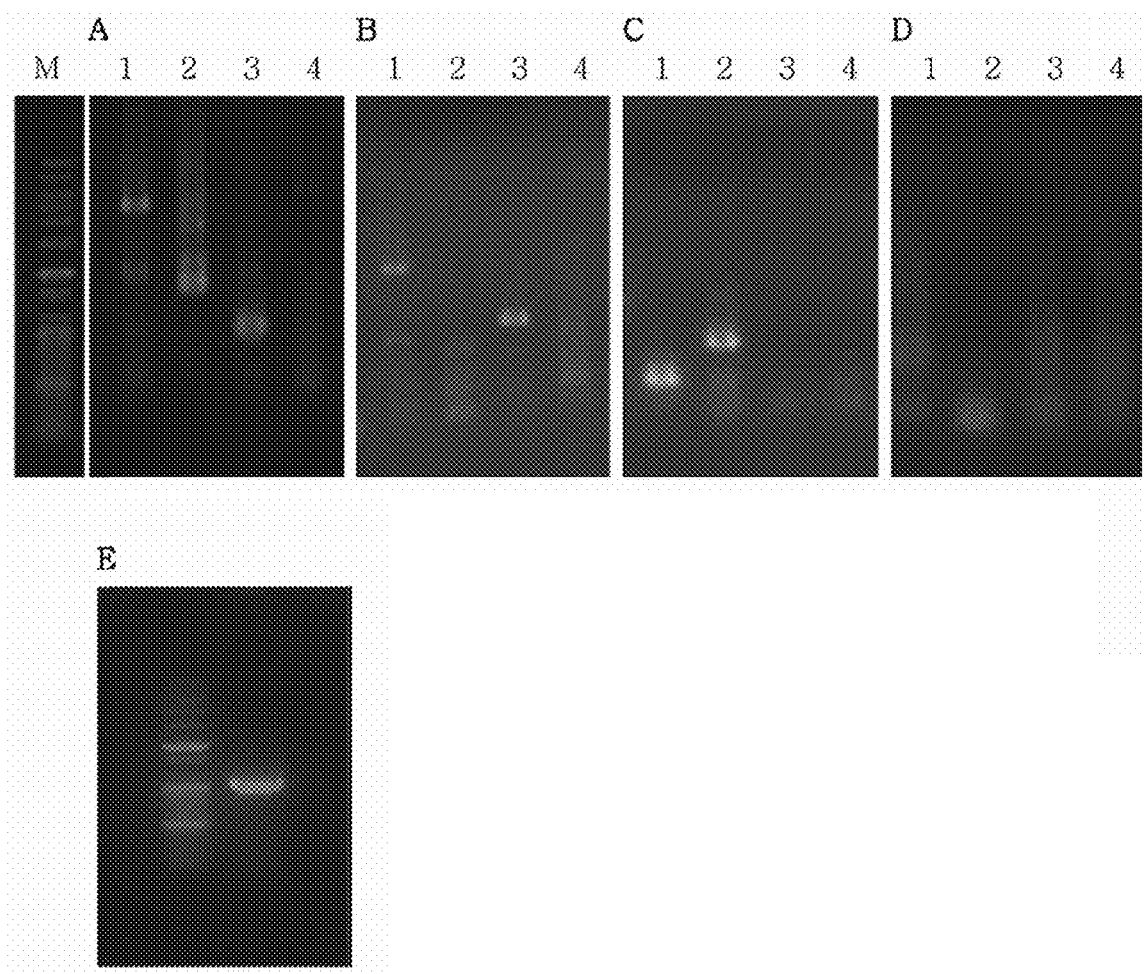
FIG. 2 illustrates a genome-walking PCR for isolating SlHD-2 promoter region. A to D; genome-walking PCR product from each of round 1 to round 4. E; PCR product of SlHD-2 promoter with full length of 940 bp (M; size marker, 1 to 4; Solanum lycopersicum DNA library treated with EcoRV, DraI, PvuII, and StuI, respectively).
Figure 5:
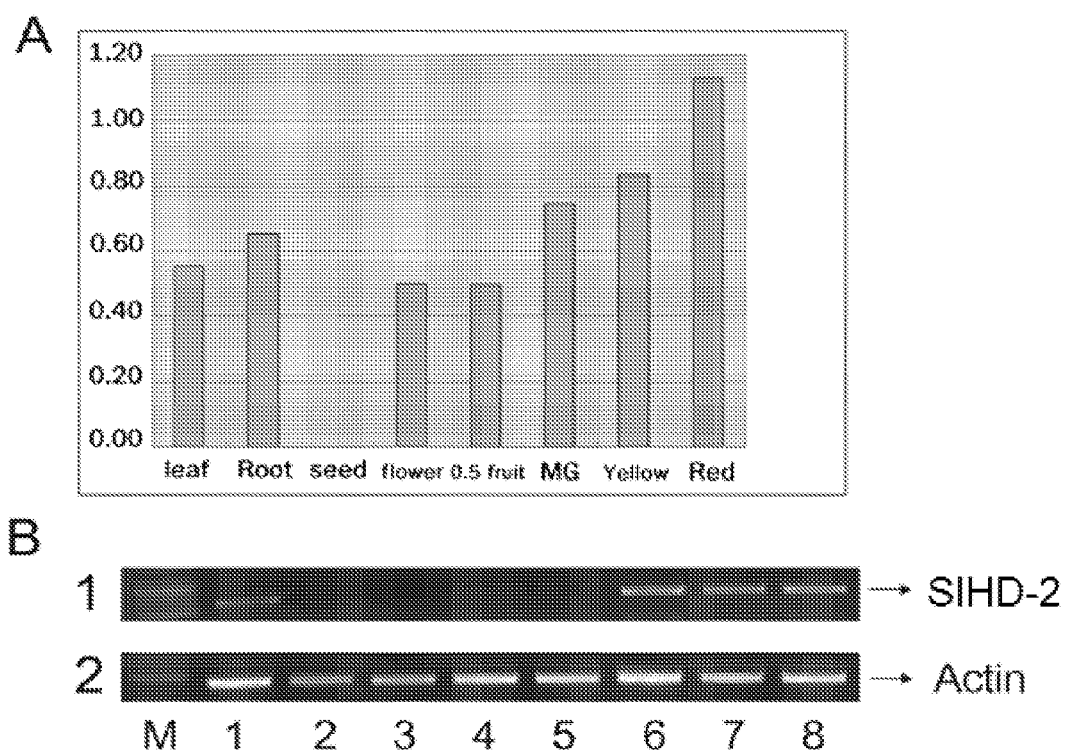
FIG. 5 illustrates SlHD-2 gene expression in Solanum lycopersicum tissue. (A) Real time PCR result showing the expression level of SlHD-2 gene at each development stage of tissue and fruit of Solanum lycopersicum. The values given are the relative expression level of—SlHD-2 when the actin expression in the leaf is set to 1. (B) Results of RT-PCR for (1); leaf, (2); root, (3); seed, (4); flower, (5); green fruit (0.5 cm), (6); MG, (7); yellow fruit, and (8); red fruit. Actin gene of Solanum lycopersicum was a positive control.

From the four rounds of the genome walking PCR, 156 bp untranslated region (5' UTR) and 784 bp promoter region of SlHD-2 were identified (A, B, C, and D of FIG. 2). Based on this result, a contig base sequence was constructed and SlHD Fwd/Rvs primer was produced. By using the primer, the promoter region (about 940 bp) comprising 5' UTR from *Solanum lycopersicum* genomic DNA was amplified (E of FIG. 2). The amplified SlHD-2 promoter region was cloned in the pGEM-T vector. After identifying the nucleotide sequence, the promoter region of SlHD-2 was analyzed based on PLANTCARE (www.plantcare.com) system. As a result, various cis-acting elements were found. The minimal promoter region is presumably located between CAT box and TATA box, that are found at −70 and −30 position, respecripe stage, wherein the expression amount is higher than that of actin (see, FIG. 5). Thus, it was found that SlHD-2 gene is expressed in a fruit-specific manner, and its expression increases according to progress of maturation of fruit.

Example 4

Southern Blot Hybridization

Figure 6:
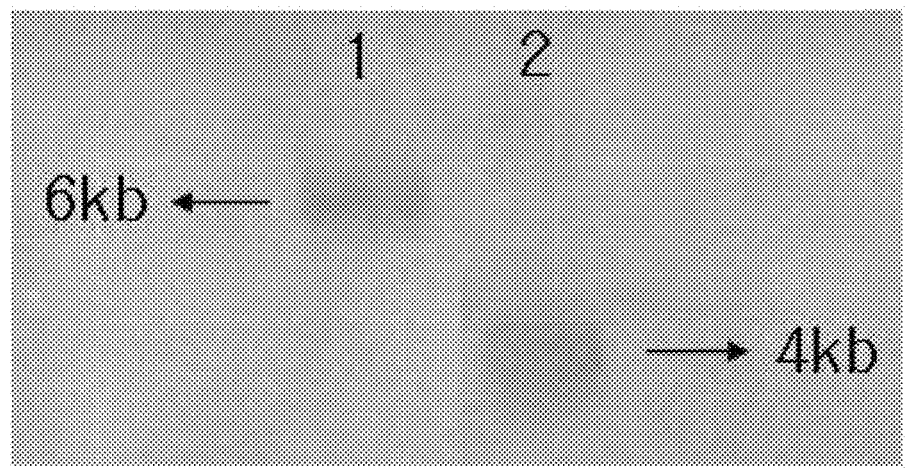
FIG. 6 illustrates a Southern blot hybridization. The DNA blot of a genomic DNA isolated from Solanum lycopersicum was hybridized with a 500 bp SlHD-2 promoter probe. The arrows shown in lane 1 and lane 2 indicate a SlHD-2 promoter-specific band. Each lane comprises 10 ug of genomic DNA, which has been digested with HindIII (lane 1) or EcoRI (lane 2).

There are many families of Histidine decarboxylase in *Solanum lycopersicum*. To find out the copy number of SlHD-2 promoter in the genome of *Solanum lycopersicum*, Southern blot analysis was carried out. From the sample treated with HindIII, a single band was identified at 6 kb position, while another band is shown at 4 kb position from the sample treated with EcoRI (see, FIG. 6). This result suggests that there is only a single copy of SlHD-2 gene promoter in the *Solanum lycopersicum* genome.

Example 5

Analysis of SlHD-2 Promoter Activity

SlHD-2 gene promoter region was amplified and cloned in pCAMBIA2300-GFP plasmid wherein hexa-histidine tail is fused at the C-terminus of GFP, yielding pCAM-2300HD vector for analysis of promoter activity (FIG. 4). The *Agrobacterium* comprising the recombinant pCAM-2300HD vector was inoculated to the *Solanum lycopersicum* tissue according to Agro-infiltration method. 2 to 3 days later, the amount of GFP that is transiently expressed in the plant tissue was determined. Specifically, the expression amount of GFP gene (pCAMBIA 1302) under the regulation of CaMV35S in each tissue was set to 1.00 and the relative activity of SlHD-2 promoter was analyzed. As a result, it was found that, in the leaf tissue, the activity of SlHD-2 is about 0.5 times lower than 35S promoter, while it is about 2 times higher in the fruit at red ripe stage (see, FIG. 7 A). Further, the expression amount in the fruit at red ripe stage is about 2.5 times higher than the leaf tissue. Considering that the activity of $^{35}S$ is only 50% in the fruit at red ripe stage compared to the leaf stage, the result above indicates that the SlHD-2 is expressed in a fruit-specific manner (see, FIG. 7 B), Example 6

Determination of Active Region of Promoter Based on Deletion Analysis

Figure 8:
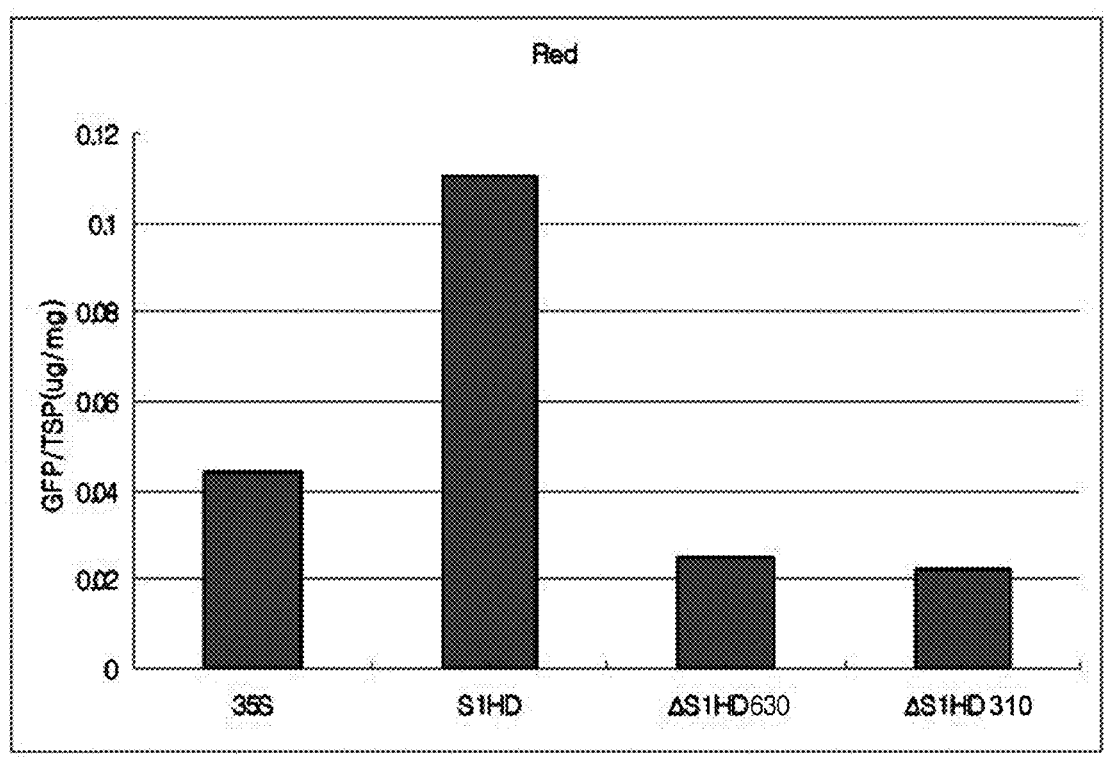
FIG. 8 shows that, in the transient expression by Agro-infiltration, the level of GFP expression by using full length SlHD-2 promoter or a partially deleted promoter of ΔSlHD630 and ΔSlHD310 is comparable to the expression in a fully-ripen fruit of Solanum lycopersicum that is obtained by using CaMV 35S promoter. The values given indicate an average value, and each construct was sampled in triplicate (GFP; green fluorescent protein, TSP; total soluble protein, mg; matured green stage of a Solanum lycopersicum fruit).

In order to determine the active region of the promoter, deletion analysis was carried out. First, ΔSlHD630 promoter in which 304 bp at 5' upstream region of the promoter (about 940 bp) comprising 156 bp 5' UTR is deleted and ΔSlHD310 promoter in which 629 bp at 5' upstream region of the promoter is deleted are cloned in pCAM2300-GFP, and the activity of the promoter in the tissue of *Solanum lycopersicum* fruit at red ripe stage was examined according to a transient expression method. As a result, it was found that the promoter activity is highest in the full-length SlHD-2 promoter. For the promoters with deleted region, the expression amount is deceased by 80% or more. Further, comparing ΔSlHD630 to ΔSlHD310, no difference in promoter activity was found (see, FIG. 8). It is believed that these results suggest possible presence of a cis-acting element showing fruit-specificity around region of from −784 to −304 of the SlHD-2 promoter.

What is claimed is:

1. An isolated fruit-specific plant expression promoter which comprises the nucleotide sequence as set forth from nucleotide base number 1 to number 481 of SEQ ID NO: 1, or the nucleotide sequence as set forth from nucleotide base number 1 to number 784 of SEQ ID NO: 1, wherein said promoter is operatively linked to a foreign gene downstream of said promoter.

2. The fruit-specific plant expression promoter according to claim 1, wherein the fruit-specific plant expression promoter comprises the nucleotide sequence as set forth from nucleotide base number 1 to number 784 of SEQ ID NO: 1.

3. A fruit-specific plant expression vector which comprises a fruit-specific plant expression promoter comprising:
   the nucleotide sequence as set forth from nucleotide base number 1 to number 481 of SEQ ID NO: 1 or the nucleotide sequence as set forth from nucleotide base number 1 to number 784 of SEQ ID NO: 1; and
   optionally a 5'-UTR comprising the nucleotide sequence as set forth from nucleotide base number 785 to number 940 of SEQ ID NO: 1.

4. The fruit-specific plant expression vector according to claim 3, wherein the fruit-specific plant expression vector is pCAM-2300HD.

5. *Agrobacterium tumefaciens* transformed with the fruit-specific plant expression vector of claim 3.

6. A plant which is transformed with the fruit-specific plant expression vector of claim 3.

7. The transformed plant according to claim 6, wherein the plant is a dicot plant.

8. A process for fruit-specific expression of a foreign gene in a transformed plant comprising:
   forming a recombinant plant expression vector by inserting a foreign gene into the fruit-specific plant expression vector of claim 3, and
   transforming a plant with the recombinant plant expression vector.

9. The process according to claim 8, wherein the plant is a dicot plant.

10. A transformed plant prepared by the process of claim 8, wherein the foreign gene is expressed in a fruit-specific manner.

11. The fruit-specific plant expression vector of claim 3, wherein the fruit-specific plant expression promoter comprises the nucleotide sequence as set forth from nucleotide base number 1 to number 481 of SEQ ID NO: 1.

12. The fruit-specific plant expression vector of claim 3, wherein the fruit-specific plant expression promoter comprises the nucleotide sequence as set forth from nucleotide base number 1 to number 784 of SEQ ID NO: 1.

* * * * *

SEQUENCE LISTING

<160> NUMBER OF SEQ ID NOS: 17

<210> SEQ ID NO 1
<211> LENGTH: 940
<212> TYPE: DNA
<213> ORGANISM: Solanum lycopersicum

<400> SEQUENCE: 1

```
agccactata tttattttac attattaatt tgccatttta tataattatt ccaatacaat      60
taaatttcca caaaatttaa gtgtgcaatc gacaaaataa atgagacatg aagggagtgt     120
ttggtaaaac gaaaaatgtt tttcatataa gaatgccttt tagaataagt gggttatttt     180
tttatttttt attttgtatt tagtacataa ttattttttt tcatcttaaa catgtattat     240
taaatataat ttaaataaaa actatgagag atgaagatag agggacgggg atgaagatga     300
ggtgcattga aaggtgtgga ttactaccaa ttaaaatgtt agtaacttgt tttcccaact     360
ttcattaatt attccctatt tttttaaaga attgacgaac tgaacctaag actcctatct     420
cctaattatt aagggagaaa aaatgaaata tttttcaag tttacgttat tttcaaagtt     480
ttagatattt tccgttaaca tgttcaacat aacagtgatg aaatttaaga ttcaccacac     540
aaaagttaag aaggcaaagc aattttttgtt gttataaatt gaaggttcca aggataatga     600
gactcacaaa acttttatct ctttaatttg aggcaattat tctcatctca aattattaca     660 attttagct ctattaggat gggaactgaa agtgtacgta atatttatgc tcaattttct     720
agttttctct tttatatact cattcattca ttttaaatca tactagtaca ttatatatta     780 aatttaatt ttttgtgtga ttatgaaata ggaatttgac tcaacagtag tcgcaacaaa     840
aactggaatc aacgcaccat tgtcatctcc aagggacaat atgtgtctta gtttgattga     900
acctcatatt aagaataaaa catcttccga agaattgaac                           940
```

<210> SEQ ID NO 2
<211> LENGTH: 22

```
<212> TYPE: DNA
<213> ORGANISM: Artificial Sequence
<220> FEATURE:
<223> OTHER INFORMATION: AP1 primer

<400> SEQUENCE: 2
gtaatacgac tcactatcgg gc                                        22

<210> SEQ ID NO 3
<211> LENGTH: 19
<212> TYPE: DNA
<213> ORGANISM: Artificial Sequence
<220> FEATURE:
<223> OTHER INFORMATION: AP2 primer

<400> SEQUENCE: 3
actatagggc acgcgtggt                                            19

<210> SEQ ID NO 4
<211> LENGTH: 27
<212> TYPE: DNA
<213> ORGANISM: Artificial Sequence
<220> FEATURE:
<223> OTHER INFORMATION: 1 Round PCR GSP1 primer

<400> SEQUENCE: 4
aatgccacaa ggcattggac atcccaa                                   27

<210> SEQ ID NO 5
<211> LENGTH: 28
<212> TYPE: DNA
<213> ORGANISM: Artificial Sequence
<220> FEATURE:
<223> OTHER INFORMATION: 1 Round PCR GSP2 primer

<400> SEQUENCE: 5
catcccaaga atttgtgccc tgaaattg                                  28

<210> SEQ ID NO 6
<211> LENGTH: 26
<212> TYPE: DNA
<213> ORGANISM: Artificial Sequence
<220> FEATURE:
<223> OTHER INFORMATION: 2 Round PCR GSP1 primer

<400> SEQUENCE: 6
atggagattg ccctcagtgc caccac                                    26

<210> SEQ ID NO 7
<211> LENGTH: 30
<212> TYPE: DNA
<213> ORGANISM: Artificial Sequence
<220> FEATURE:
<223> OTHER INFORMATION: 2 Round PCR GSP2 primer

<400> SEQUENCE: 7
ctgtagggtg ctgagtaaag gggtctccac                                30

<210> SEQ ID NO 8
<211> LENGTH: 26
<212> TYPE: DNA
<213> ORGANISM: Artificial Sequence
<220> FEATURE:
<223> OTHER INFORMATION: 3 Round PCR GSP1 primer

<400> SEQUENCE: 8
gaggagagag gcgagcgaga gagggt                                    26
```

<210> SEQ ID NO 9
<211> LENGTH: 34
<212> TYPE: DNA
<213> ORGANISM: Artificial Sequence
<220> FEATURE:
<223> OTHER INFORMATION: 3 Round PCR GSP2 primer

<400> SEQUENCE: 9
tctctatctc catgcggtag agaggttgtg tctt                                34

<210> SEQ ID NO 10
<211> LENGTH: 25
<212> TYPE: DNA
<213> ORGANISM: Artificial Sequence
<220> FEATURE:
<223> OTHER INFORMATION: 4 Round PCR GSP1 primer

<400> SEQUENCE: 10
cgttgattcc agtttttgtt gcgac                                          25

<210> SEQ ID NO 11
<211> LENGTH: 30
<212> TYPE: DNA
<213> ORGANISM: Artificial Sequence
<220> FEATURE:
<223> OTHER INFORMATION: 4 Round PCR GSP2 primer

<400> SEQUENCE: 11
aatttaatat ataatgtact agtatgattt                                     30

<210> SEQ ID NO 12
<211> LENGTH: 27
<212> TYPE: DNA
<213> ORGANISM: Artificial Sequence
<220> FEATURE:
<223> OTHER INFORMATION: S1HD Forward primer

<400> SEQUENCE: 12
taagcttagc cactatattt attttac                                        27

<210> SEQ ID NO 13
<211> LENGTH: 27
<212> TYPE: DNA
<213> ORGANISM: Artificial Sequence
<220> FEATURE:
<223> OTHER INFORMATION: S1HD Reverse primer

<400> SEQUENCE: 13
aggatccgtt caattcttcg gaagatg                                        27

<210> SEQ ID NO 14
<211> LENGTH: 24
<212> TYPE: DNA
<213> ORGANISM: Artificial Sequence
<220> FEATURE:
<223> OTHER INFORMATION: S1HD630 primer

<400> SEQUENCE: 14
taagcttcat tgaaaggrgr ggat                                           24

<210> SEQ ID NO 15
<211> LENGTH: 25
<212> TYPE: DNA
<213> ORGANISM: Artificial Sequence
<220> FEATURE:
<223> OTHER INFORMATION: S1HD310 primer -continued

```
<400> SEQUENCE: 15
taagcttgag gcaattattc tcatc                                         25

<210> SEQ ID NO 16
<211> LENGTH: 22
<212> TYPE: DNA
<213> ORGANISM: Artificial Sequence
<220> FEATURE:
<223> OTHER INFORMATION: Forward primer

<400> SEQUENCE: 16
cattgcgatg cagcattatg tg                                            22

<210> SEQ ID NO 17
<211> LENGTH: 24
<212> TYPE: DNA
<213> ORGANISM: Artificial Sequence
<220> FEATURE:
<223> OTHER INFORMATION: Reverse primer

<400> SEQUENCE: 17
ttcaagtcat ggtrtccaag gagt                                          24
```